US008648299B2

(12) United States Patent
Notte, IV et al.

(10) Patent No.: US 8,648,299 B2
(45) Date of Patent: Feb. 11, 2014

(54) ISOTOPE ION MICROSCOPE METHODS AND SYSTEMS

(71) Applicants: John A. Notte, IV, Gloucester, MA (US); Sybren Sijbrandij, Wakefield, MA (US)

(72) Inventors: John A. Notte, IV, Gloucester, MA (US); Sybren Sijbrandij, Wakefield, MA (US)

(73) Assignee: Carl Zeiss Microscopy, LLC, Thornwood, NY (US)

( * ) Notice: Subject to any disclaimer, the term of this patent is extended or adjusted under 35 U.S.C. 154(b) by 0 days.

(21) Appl. No.: 13/783,534

(22) Filed: Mar. 4, 2013

(65) Prior Publication Data

US 2013/0175444 A1    Jul. 11, 2013

Related U.S. Application Data

(63) Continuation of application No. 12/999,683, filed as application No. PCT/US2009/045133 on May 26, 2009, now Pat. No. 8,399,834.

(60) Provisional application No. 61/074,209, filed on Jun. 20, 2008.

(51) Int. Cl.
*G01N 23/225* (2006.01)
*H01J 37/317* (2006.01)
*H01J 37/30* (2006.01)

(52) U.S. Cl.
USPC ........... 250/307; 250/306; 250/309; 250/283; 250/492.21; 250/492.3

(58) Field of Classification Search
USPC .......... 250/307, 306, 309, 283, 492.21, 492.3
See application file for complete search history.

(56) References Cited

U.S. PATENT DOCUMENTS

| 4,226,666 | A | 10/1980 | Winters et al. ................. 156/643 |
| 4,426,576 | A * | 1/1984 | Hurst et al. .................... 250/283 |
| H147 | H | 11/1986 | Feldman et al. ................. 357/47 |
| 4,658,135 | A | 4/1987 | Allman et al. ................. 250/283 |
| 4,694,167 | A | 9/1987 | Payne et al. .................... 250/282 |
| 5,087,815 | A * | 2/1992 | Schultz et al. .................. 850/63 |
| 7,804,068 | B2 | 9/2010 | Notte, IV ....................... 250/309 |
| 8,059,779 | B2 | 11/2011 | Greatbatch .................... 376/147 |
| 8,093,563 | B2 | 1/2012 | Rahman et al. ........... 250/396 R |
| 8,109,865 | B2 | 2/2012 | Jackson ........................... 600/1 |
| 8,399,834 | B2 * | 3/2013 | Notte et al. ..................... 250/309 |
| 2007/0158558 | A1 | 7/2007 | Ward et al. |
| 2007/0158580 | A1 | 7/2007 | Ward et al. .................... 250/426 |

(Continued)

FOREIGN PATENT DOCUMENTS

| JP | 0720068 | 1/1995 | ........... G01N 23/203 |
| JP | 2002214398 | 7/2002 | ............... G21K 5/04 |
| WO | 2009/114230 | 9/2009 | |

OTHER PUBLICATIONS

Isshiki et al., "Activation Analysis of Oxygen in Iron and Chromium Through Bombardment by ³He Ion Beam", Transactions of the Iron and Steel Institute of Japan, vol. 23, No. 9, pp. 796-799, 1983.

(Continued)

*Primary Examiner* — Nikita Wells
(74) *Attorney, Agent, or Firm* — Fish & Richardson P.C.

(57) ABSTRACT

Ion microscope methods and systems are disclosed. In general, the systems and methods involve relatively light isotopes, minority isotopes or both. In some embodiments, an isotope of Neon is used.

18 Claims, 2 Drawing Sheets

(56) References Cited

U.S. PATENT DOCUMENTS

| | | | |
|---|---|---|---|
| 2009/0026879 A1 | 1/2009 | Prelas | 310/303 |
| 2009/0162278 A1 | 6/2009 | Ravn et al. | 424/1.37 |
| 2010/0051805 A1 | 3/2010 | Rahman et al. | 250/307 |
| 2011/0049364 A1 | 3/2011 | Knippelmeyer et al. | |
| 2011/0215238 A1 | 9/2011 | Kajihara | 250/282 |
| 2012/0097849 A1 | 4/2012 | Rahman et al. | 250/307 |
| 2012/0141693 A1 | 6/2012 | Ward et al. | 427/585 |

OTHER PUBLICATIONS

Japanese Office Action, Japanese Application No. 2011-514670, with an English Summary, 5 pages, dated Jul. 23, 2013.

Tabasso et al., "Observations of hydrocarbon film deposition in the MAST tokamak," *J of Nuclear Materials*, vol. 306, No. 1, Nov. 2002, pp. 73-77.

Nozaki et al., "Helium-3 activation of oxygen in silicon nitride films on silicon wafers," *J Radioanalytical Chemistry*, vol. 52, No. 2, Sep. 2, 1979, pp. 449-459.

Livengood et al., "Helium ion microscope invasiveness and imaging study for semiconductor applications," *J. Vac. Sci. Technolog. B*, vol. 25, No. 6, Nov. 2007, pp. 2547-2552.

International Search Report and Written Opinion for PCT Application No. PCT/US2009/045133, dated Jan. 15, 2010.

Kuo, H., et al., "Gas field ion source from an Ir/W<111> single-atom tip" Appl. Phys. Lett. 92, 063106 (2008).

* cited by examiner

ISOTOPE ION MICROSCOPE METHODS AND SYSTEMS

CROSS-REFERENCE TO RELATED APPLICATIONS

This application is a continuation of, and claims priority under 35 U.S.C. §120 to, U.S. Ser. No. 12/999,683, filed Feb. 18, 2011, which is a national phase under 35 U.S.C. §371 of International Patent Application Serial Number PCT/US2009/045133, filed May 26, 2009, which claims benefit under 35 U.S.C. §119 of U.S. Ser. No. 61/074,209, filed Jun. 20, 2008. The entire contents of each of these applications are incorporated herein by reference.

TECHNICAL FIELD

This disclosure relates to ion microscope methods and systems, particularly as they relate to relatively light isotopes, minority isotopes or both.

BACKGROUND

Ions can be used to investigate and/or modify a sample.

SUMMARY

In one aspect, the disclosure generally relates to using ions of an isotope of a noble gas to investigate and/or modify a sample. The isotope can be a relatively light isotope, a minority isotope, or both. An example of such an isotope is He-3.

In embodiments in which the ions used to investigate/modify a sample are less massive than the atoms from which the sample is formed, it is believed that, relative to sample damage that may occur when ions of a relatively heavy isotope (e.g., He-4), using ions of a relatively light isotope (e.g., He-3) can reduce the possibility of sample damage due to the interaction of the ions with sample because the energy transfer from the relatively light ions to sample atoms is less efficient than the energy transfer from the relatively heavy ions to sample atoms.

Typically, the ions pass through ion optics before interacting with the sample. Often, the ion optics include one or more beam-forming apertures. In embodiments in which the ions used to investigate/modify a sample are less massive than the atoms from which the beam-forming aperture(s) is(are) formed, it is believed that, relative to damage to the beam-forming aperture(s) that may occur when ions of a relatively heavy isotope (e.g., He-4), using ions of a relatively light isotope (e.g., He-3) can reduce the possibility of damage to beam-forming aperture(s) due to the interaction of the ions with the beam-forming aperture(s) because the energy transfer from the relatively light ions to atoms of the beam-forming aperture(s) is less efficient than the energy transfer from the relatively heavy ions to atoms of the beam-forming aperture(s).

In embodiments in which the ions used to investigate/modify a sample are less massive than the atoms from which the source tip is formed, it is believed that, relative to sample damage that may occur when ions of a relatively heavy isotope (e.g., He-4), using ions of a relatively light isotope (e.g., He-3) can reduce the possibility of source tip damage due to the interaction of the ions with source tip because the energy transfer from the relatively light atoms to source tip atoms is less efficient than the energy transfer from the relatively heavy atoms to source tip atoms.

In some embodiments, such as when particularly high doses and/or particularly high beam currents are used, ions may enter the subsurface or bulk regions of a sample, potentially resulting in formation of a gas in the subsurface or bulk region. At a given temperature, the diffusion rate of a lighter gas (e.g., He-3) from the sample can be higher than the diffusion rate from the sample of a heavier gas (e.g., He-4). Alternatively or additionally, a lighter gas (e.g., He-3) may diffuse from the sample at a lower temperature than a heavier gas (e.g., (He-4).

Assuming the potential between the source tip and the sample is held constant, ions of the lighter isotope and ions of the heavier isotope will generally have the same energy as they pass through the ion optics. However, because the speed of an ion in the ion optics is inversely proportional to the square root of the mass of the ion, the lighter ions will generally be moving faster than the heavier ions. As a result, in general, there will be less crowding of the lighter ions in the ion optics, relative to the amount of crowding that would occur with heavier ions. It is believed that, relative to an ion beam of the heavier ions, the reduced crowding present in an ion beam of the lighter ions will reduce space charge effects between the ions in the ion optics, which will result in reduced spreading of the width of the beam as measured in the plane of the sample surface.

In one aspect, the disclosure features a method that includes using ions to investigate a sample, where at least 0.01% of the ions are He-3 ions.

In another aspect, the disclosure features a method that includes using ions to investigate a sample, where at least 0.1% of the ions are He ions, and at most 99.9% of the ions are He-4 ions.

In a further aspect, the disclosure features a method that includes using a gas field ion source to generate ions, where at least 0.01% of the ions are He-3 ions.

In an additional aspect, the disclosure features a method that includes using ions of an isotope of a noble gas to investigate a sample. The isotope is selected from He-3, Ne-21, Ne-22, Ar-36, Ar-38, Kr-78, Kr-80, Kr-82, Kr-83, Xe-124, Xe-126, Xe-128, Xe-129, Xe-130, Xe-131, Xe-132, Xe-134 and/or Xe-136. A percentage of the ions is greater than a natural abundance of the isotope.

In one aspect, the disclosure features a method that includes using ions to modify a sample, where at least 0.01% of the ions are He-3 ions.

In another aspect, the disclosure features a method that includes using ions to modify a sample, where at least 0.1% of the ions are He ions, and at most 99.9% of the ions are He-4 ions.

In a further aspect, the disclosure features a method that includes using ions of an isotope of a noble gas to modify a sample. The isotope is selected from He-3, Ne-21, Ne-22, Ar-36, Ar-38, Kr-78, Kr-80, Kr-82, Kr-83, Xe-124, Xe-126, Xe-128, Xe-129, Xe-130, Xe-131, Xe-132, Xe-134 and/or Xe-136. The percentage of the ions is greater than a natural abundance of the isotope.

In an additional aspect, the disclosure features a method that includes using ions to investigate a sample. At least 0.01% of the ions are ions of Ne-21, Ne-22, Ar-36, Ar-38, Kr-78, Kr-80, Kr-82, Kr-83, Xe-124, Xe-126, Xe-128, Xe-129, Xe-130, Xe-131, Xe-132, Xe-134 and/or Xe-136.

In one aspect, the disclosure features a method that includes using a gas field ion source to generate an ion beam comprising ions. At least 0.01% of the ions in the ion beam are ions of Ne-21, Ne-22, Ar-36, Ar-38, Kr-78, Kr-80, Kr-82, Kr-83, Xe-124, Xe-126, Xe-128, Xe-129, Xe-130, Xe-131, Xe-132, Xe-134 and/or Xe-136.

In another aspect, the disclosure features a method that includes using ions to modify a sample. At least 0.01% of the ions are ions of Ne-21, Ne-22, Ar-36, Ar-38, Kr-78, Kr-80, Kr-82, Kr-83, Xe-124, Xe-126, Xe-128, Xe-129, Xe-130, Xe-131, Xe-132, Xe-134 and/or Xe-136.

In a further aspect, the disclosure features a method that includes forming a first ion beam that a first percentage of ions that are He-3 ions, and using a field to modify the first ion beam to form a second ion beam having a second percentage of ions that are He-3 ions. The first percentage is different from the second percentage.

In additional aspect, the disclosure features a method that includes forming a first ion beam having a first percentage of an isotope of a noble gas, and using a field to modify the first ion beam to form a second ion beam having a second percentage of the isotope of the noble gas. The first percentage is different from the second percentage. The isotope is selected from Ne-21, Ne-22, Ar-36, Ar-38, Kr-78, Kr-80, Kr-82, Kr-83, Xe-124, Xe-126, Xe-128, Xe-129, Xe-130, Xe-131, Xe-132, Xe-134 and/or Xe-136.

In one aspect, the disclosure features a method that includes using an ion beam to investigate a sample. The ion beam includes at least 0.1% He ions, and less than 99.9% of the He ions are He-4 ions.

In another aspect, the disclosure features a method that includes using an ion beam to modify a sample. The ion beam includes at least 0.1% He ions, and less than 99.9% of the He ions are He-4 ions.

In a further aspect, the disclosure features a method that includes using an ion beam to investigate a sample. The ion beam includes at least 0.1% Ne ions, and less than 90% of the Ne ions are Ne-20 ions.

In an additional aspect, the disclosure features a method that includes using an ion beam to investigate a sample. The ion beam includes at least 0.1% Ar ions, and less than 99.5% of the Ar ions are Ar-40 ions.

In one aspect, the disclosure features a method that includes using an ion beam to investigate a sample. The ion beam includes at least 0.1% Kr ions, and less than 55% of the Kr ions are Kr-84 ions.

In another aspect, the disclosure features a method that includes using an ion beam to investigate a sample. The ion beam includes at least 0.1% Xe ions, and less than 25% of the Xe ions are Xe-132 ions.

In a further aspect, the disclosure features a method that includes using an ion beam to modify a sample. The ion beam includes at least 0.1% Ne ions, and less than 90% of the Ne ions are Ne-20 ions.

In an additional aspect, the disclosure features a method that includes using an ion beam to modify a sample. The ion beam includes at least 0.1% Ar ions, and less than 99.5% of the Ar ions are Ar-40 ions.

In one aspect, the disclosure features a method that includes using an ion beam to modify a sample. The ion beam includes at least 0.1% Kr ions, and less than 55% of the Kr ions are Kr-84 ions.

In another aspect, the disclosure features a method that includes using an ion beam to modify a sample. The ion beam includes at least 0.1% Xe ions, and less than 25% of the Xe ions are Xe-132 ions.

Other features and advantages will be apparent from the description, drawings, and claims.

DESCRIPTION OF DRAWINGS

Like reference symbols in the various drawings indicate like elements.

DETAILED DESCRIPTION

Ion Microscope

Figure 1:
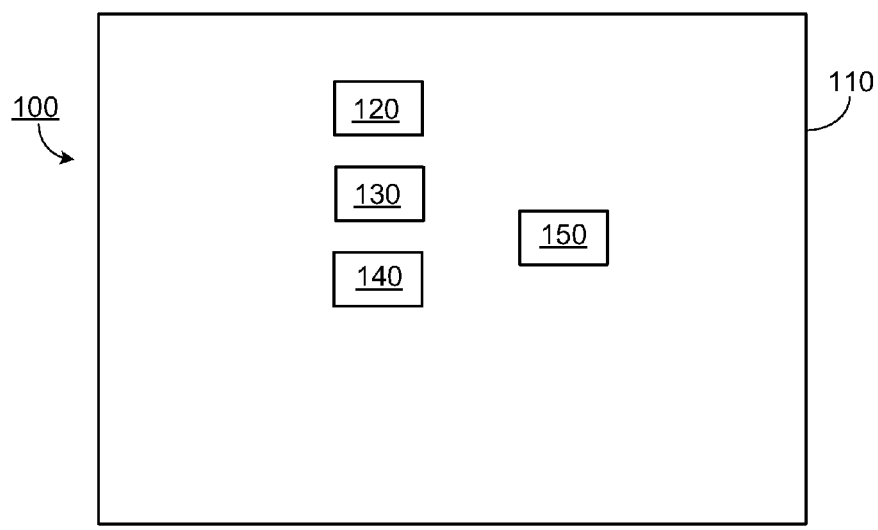
FIG. 1 is a schematic representation of an ion microscope.

FIG. 1 is a schematic representation of an ion microscope 100 that may be used to investigate and/or modify a sample. Ion microscope 100 includes a housing 110, a gas field ion source 120, ion optics 130, a sample 140 and a detector 150. During use, an isotope of a gas (e.g., He-3) is disposed in housing 110, and a relatively high positive potential is applied to a tip (e.g., an electrically conductive tip) that is part of source 120. The gas (e.g., He-3) is ionized, and the ions enter ion optics 130, which direct the ions to sample 130. The ions (e.g., He-3 ions) interact with sample 140 to generate particles, such as electrons and/or scattered ions, that are detected by detector 150. This information is used to determine one or more characteristics about sample 140, such as the topography of sample 140 and/or material constituent information about sample 140. Alternatively or additionally, the ions (e.g., He-3 ions) can be used to modify sample 140. For example, the ions (e.g., He-3 ions) can be used in a gas assisted chemistry process to form material on the surface of sample 140.

Ion microscopes are described, for example, in US 2007-0158558, which is hereby incorporated by reference in its entirety.

Isotopes

In some embodiments, the isotope is He-3. In general, any desired source of He-3 can be used. In some embodiments, commercially available He-3 gas can be used. In certain embodiments, commercially available He gas (e.g., containing approximately the natural abundance of He-3) can be used. In such embodiments, one or more processes can be used to modify the gas and/or ions formed by the gas to yield a gas and/or ions that have an amount of He-3 greater than its natural abundance. As an example, one or more fields (e.g., one or more electric fields, one or more magnetic fields, a combination of one or more magnetic fields and one or more electric fields) can be used to modify the amount of He-3 present. The fields can be generated, for example, by one or more components in the ion optics. In some embodiments, the method involves forming a first ion beam including He-3 ions, and using one or more fields to modify the first ion beam to form a second ion beam including He-3 ions. The percentage of ions in the first ion beam that are He-3 ions is different from the percentage of ions in the second ion beam that are He-3 ions. Optionally, the second ion beam can be used to investigate and/or modify a sample. The percentage of ions in the second ion beam that are He-3 ions can be, for example, at least two times (e.g., at least five times, at least 10 times, at least 25 times, at least 50 times, at least 75 times, at least 90 times, at least 95 times) the percentage of ions in the first beam that are He-3 ions. The percentage of ions in the second ion beam can that are He-3 ions can be, for example, at least 0.01% (e.g., at least 0.1%, at least 1%, at least 10%, at least 20%, at least 30%, at least 40%, at least 50%, at least 60%, at least 70%, at least 80%, at least 90%, at least 95%).

While He-3 is noted above as an example of an isotope, more generally, any isotope can be used. In general, the isotope is a relatively light isotope, a minority isotope, or both.

Typically, the isotope is an isotope of a noble gas (He, Ne, Ar, Kr, Xe). Examples of isotopes include Ne-21, Ne-22, Ar-36, Ar-38, Kr-78, Kr-80, Kr-82, Kr-83, Xe-124, Xe-126, Xe-128, Xe-129, Xe-130, Xe-131, Xe-132, Xe-134 and Xe-136. Table I lists certain isotopes and corresponding natural abundances (approximate values due to rounding).

TABLE I

| Isotope | Natural Abundance |
|---|---|
| He-4 | 99.99986 |
| He-3 | 0.00014 |
| Ne-20 | 0.905 |
| Ne-21 | 0.003 |
| Ne-22 | 0.092 |
| Ar-36 | 0.003 |
| Ar-38 | 0.001 |
| Ar-40 | 0.996 |
| Kr-78 | 0.004 |
| Kr-80 | 0.023 |
| Kr-82 | 0.116 |
| Kr-83 | 0.115 |
| Kr-84 | 0.570 |
| Kr-86 | 0.173 |
| Xe-124 | 0.001 |
| Xe-126 | 0.001 |
| Xe-128 | 0.019 |
| Xe-129 | 0.264 |
| Xe-130 | 0.041 |
| Xe-131 | 0.212 |
| Xe-132 | 0.269 |
| Xe-134 | 0.104 |
| Xe-136 | 0.089 |

In certain embodiments, the percentage of ions in the beam that are formed of the isotope (e.g., as measured as the percentage of ions in the ion beam that are formed of the isotope) is greater than the natural abundance of the isotope. For example, in some embodiments, the percentage of ions in the beam that are formed of the isotope is at least two times (e.g., at least five times, at least 10 times, at least 25 times, at least 50 times, at least 100 times, at least 1000 times) the natural abundance of the isotope.

In some embodiments, at least 0.01% (e.g., at least 0.1%, at least 1%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%) of the ions in the ion beam are ions of the isotope.

In certain embodiments, at least 0.01% (e.g., at least 0.1%, at least 1%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%) of the gas used to form the ion beam is the isotope.

In some embodiments, at least 0.1% (e.g., at least 1%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%) of the gas used to form the ion beam is the isotope, and/or at most 99.9% (e.g., at most 99%, at most 90%, at most 85%, at most 80%, at most 75%, at most 70%, at most 65%, at most 60%, at most 55%, at most 50%, at most 45%, at most 40%, at most 35%, at most 30%, at most 25%, at most 20%, at most 15%, at most 10%, at most 5%, at most 1%) of the gas used to form the ion beam is the isotope. As an example, in some embodiments, one isotope is He-3 and the other isotope is He-4.

In certain embodiments, at least 0.1% (e.g., at least 1%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%) of the ions in the ion beam are ions of the isotope, and/or at most 99.9% (e.g., at most 99%, at most 90%, at most 85%, at most 80%, at most 75%, at most 70%, at most 65%, at most 60%, at most 55%, at most 50%, at most 45%, at most 40%, at most 35%, at most 30%, at most 25%, at most 20%, at most 15%, at most 10%, at most 5%, at most 1%) of the ions in the ion beam are the isotope. As an example, in some embodiments, one isotope is He-3 and the other isotope is He-4.

Particles and Particle Detection

Various types of particles can be detected with detector 150. Examples of particles include secondary electrons, Auger electrons, secondary ions, secondary neutral particles, primary neutral particles, scattered ions and photons. As referred to herein, a scattered ion is generated when an ion from the ion beam (e.g., a He ion) interacts with the sample and is scattered from the sample while remaining an ion (e.g., a He ion). Because the probability that a scattered ion can travel from the sub-surface region of a sample to the surface of the sample and then be emitted from the sample is very low, scattered ions generally provide information about the surface of the sample. As explained in more detail below, when detecting scattered ions, the particular arrangement of the detector(s) generally depends on the type of information that is desired to be obtained. A secondary electron, as referred to herein, is an electron that is emitted from a sample species and that has an energy of less than 50 eV. In general, secondary electrons are emitted from the sample surface at a range of angles and energies. However, the information of most interest is usually the total abundance of secondary electrons (as opposed to energy-resolved secondary electron information, or angle-resolved secondary electron information) because, as explained below, the total abundance of the secondary electrons is what can provide information regarding the sample surface.

In some embodiments, detecting the total abundance of secondary electrons can provide information regarding the topography of a sample. The secondary electron total abundance at a given location on a surface generally depends upon the slope of the surface relative to the ion beam at that point. In general, the secondary electron total abundance is higher where the slope of the surface relative to the ion beam is higher (i.e., where the angle of incidence of the ion beam as measured from the surface normal is larger). Thus, the change in the total abundance of secondary electrons as a function of the location of the ion beam on the surface of the sample, can be correlated to a change in the slope of the surface, providing information regarding the topography of the surface of the sample.

Detecting the total abundance of secondary electrons can also yield material constituent information (e.g., elemental information, chemical environment information) about a sample. In such embodiments, the information is predominantly related to the surface of the sample. In general, each element or material in a given chemical environment will have a particular inherent secondary electron yield. As a result, the secondary electron total abundance at a given location on a surface generally depends on the material present at that location. Therefore, the change in the total abundance of secondary electrons as a function of the location of the ion beam on the surface of the sample, can be correlated to a change in the element(s) and/or material(s) present at the surface of the sample, providing material constituent information about the surface of the sample.

In certain embodiments, the total abundance of scattered ions can be used to determine qualitative material constituent information because, in general, the scattering probability of an ion, such as a He ion, (and therefore the total abundance of scattered ions, assuming no effects from other factors, such as topographical changes in the surface sample) is approximately proportional to the square of the atomic number (Z value) of the surface atom from which the ion scatters. Thus, as an example, when using He ions and trying to distinguish a copper (atomic number 29) line from silicon (atomic number 14) in a semiconductor article, the total abundance of scattered He ions from a copper atom at a surface of the semiconductor article will be approximately four times the total abundance of scattered ions from a silicon atom at the surface of the semiconductor article. As another example, when using He ions trying to distinguish a tungsten (atomic number 74) plug from silicon (atomic number 14) in a semiconductor article, the total abundance of scattered He ions from a tungsten atom at a surface of the semiconductor article will be approximately 25 times the total abundance of scattered ions from a silicon atom at the surface of the semiconductor article. As a further example, when using He ions trying to distinguish gold (atomic number 79) region from silicon (atomic number 14) in a semiconductor article, the total abundance of scattered He ions from a gold atom at a surface of the semiconductor article will be approximately 25 times the total abundance of scattered ions from a silicon atom at the surface of the semiconductor article. As an additional example, when using He ions and trying to distinguish indium (atomic number 49) from silicon (atomic number 14) in a semiconductor article, the total abundance of scattered He ions from an indium atom at a surface of the semiconductor article will be approximately 10 times the total abundance of scattered ions from a silicon atom at the surface of the semiconductor article.

The total abundance of scattered ions can be detected using a single detector (e.g., a hemispherical detector) configured to detect scattered ions leaving the surface of a sample, or multiple detectors (e.g., located at different solid angles with respect to the surface of the sample) configured to detect scattered ions leaving the surface of a sample.

In some embodiments, energy-resolved and angle-resolved scattered ion detection can be used to determine quantitative material constituent information about the surface of a sample. The detector is designed so that the angle and energy of each detected scattered ion is known for each angle within the acceptance angle of detector. Using He ions as an example, by measuring the energy and scattering angle of the scattered He ion, the mass of the atom at the surface that scatters the scattered He ion can be calculated based on the following relationship:

$$\frac{E_s}{E_i} = 1 - \frac{2M_{He}M_a}{(M_{He} + M_a)^2}(1 - \cos\theta_s)$$

where $E_s$ is the energy of the scattered He ion, $E_i$ is the incident energy of the He ion, $M_{He}$ is the mass of the He ion, $\theta_s$ is the scattering angle, and $M_a$ is the mass of the atom that scatters the He ion.

The detector can, for example, be an energy-resolving phosphor-based detector, an energy-resolving scintillator-based detector, a solid state detector, an energy-resolving electrostatic prism-based detector, an electrostatic prism, an energy-resolving ET detector, or an energy-resolving microchannel. In general, it is desirable for the detector to have a substantial acceptable angle. In some embodiments, the detector is stationary (e.g., an annular detector). In certain embodiments, the detector can sweep through a range of solid angles. Although a system for detecting energy-resolved and angle-resolved scattered ions that includes a single detector has been described above, such a system can contain multiple (e.g., two, three, four, five, six, seven, eight) detectors. Often, the use of multiple detectors is desirable because it can allow for a larger acceptance angle of detected scattered ions.

Particles and particle detection are described, for example, in US 2007-0158558.

Detectors

Examples of detectors include Everhart-Thornley (ET) detectors, microchannel plate detectors, conversion plates, channeltron detectors, phosphor detectors and solid state detectors. The detectors can be used to detect one or more of the types of particles noted above. In some embodiments, a detector (e.g., a prism detector, a solid state detector) can be used to detect the energy of a particle (e.g., an electron, a scattered ion).

Detectors are described, for example, in US 2007-0158558.

Samples, Sample Inspection and Sample Modification

An example of a sample is a semiconductor article. Semiconductor fabrication typically involves the preparation of an article (a semiconductor article) that includes multiple layers of materials sequentially deposited and processed to form an integrated electronic circuit, an integrated circuit element, and/or a different microelectronic device. Such articles typically contain various features (e.g., circuit lines formed of electrically conductive material, wells filled with electrically non-conductive material, regions formed of electrically semi-conductive material) that are precisely positioned with respect to each other (e.g., generally on the scale of within a few nanometers). The location, size (length, width, depth), composition (chemical composition) and related properties (conductivity, crystalline orientation, magnetic properties) of a given feature can have an important impact on the performance of the article. For example, in certain instances, if one or more of these parameters is outside an appropriate range, the article may be rejected because it cannot function as desired. As a result, it is generally desirable to have very good control over each step during semiconductor fabrication, and it would be advantageous to have a tool that could monitor the fabrication of a semiconductor article at various steps in the fabrication process to investigate the location, size, composition and related properties of one or more features at various stages of the semiconductor fabrication process. As used herein, the term semiconductor article refers to an integrated electronic circuit, an integrated circuit element, a microelectronic device or an article formed during the process of fabricating an integrated electronic circuit, an integrated circuit element, a microelectronic device. In some embodiments, a semiconductor article can be a portion of a flat panel display or a photovoltaic cell. Regions of a semiconductor article can be formed of different types of material (electrically conductive, electrically non-conductive, electrically semiconductive). Exemplary electrically conductive materials include metals, such as aluminum, chromium, nickel, tantalum, titanium, tungsten, and alloys including one or more of these metals (e.g., aluminum-copper alloys). Metal silicides (e.g., nickel silicides, tantalum silicides) can also be electrically conductive. Exemplary electrically non-conductive materials include borides, carbides, nitrides, oxides, phosphides, and sulfides of one or more of the metals (e.g., tantalum borides, tantalum germaniums, tantalum nitrides, tantalum silicon nitrides, and titanium nitrides). Exemplary electrically semiconductive materials include silicon, germanium and gallium arsenide. Optionally, an electrically semiconductive material can be doped (p-doped, n-doped) to enhance the electrical conductivity of the material. Typical steps in the deposition/processing of a given layer of material include imaging the article (e.g., to determine where a desired feature to be formed should be located), depositing an appropriate material (e.g., an electrically conductive material, an electrically semiconductive material, an electrically non-conductive material) and etching to remove unwanted material from certain locations in the article. Often, a photoresist, such as a polymer photoresist, is deposited/exposed to appropriate radiation/selectively etched to assist in controlling the location and size of a given feature. Typically, the photoresist is removed in one or more subsequent process steps, and, in general, the final semiconductor article desirably does not contain an appreciable amount of photoresist.

Figure 2A:
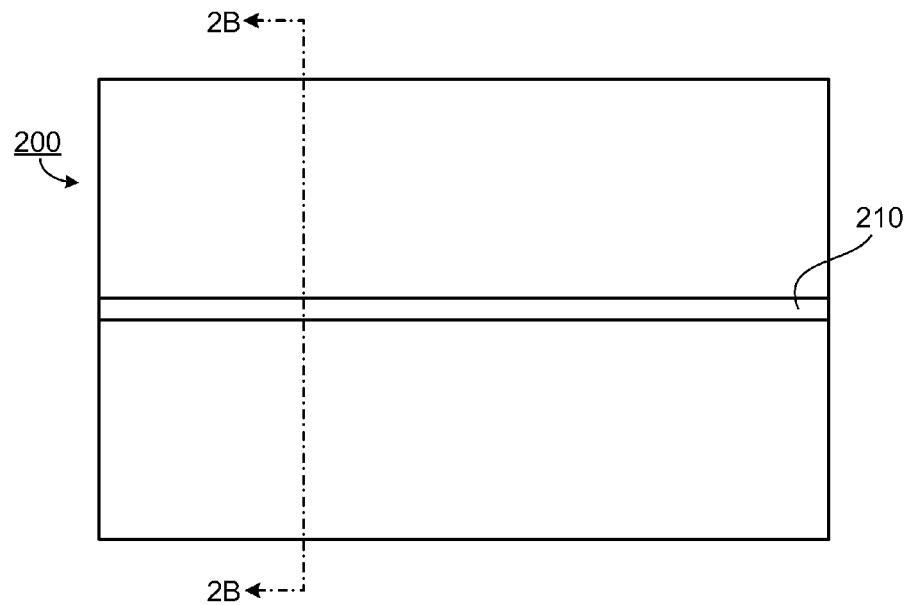
FIGS. 2A and 2B are top and cross-sectional views, respective, of a sample.
Figure 2B:
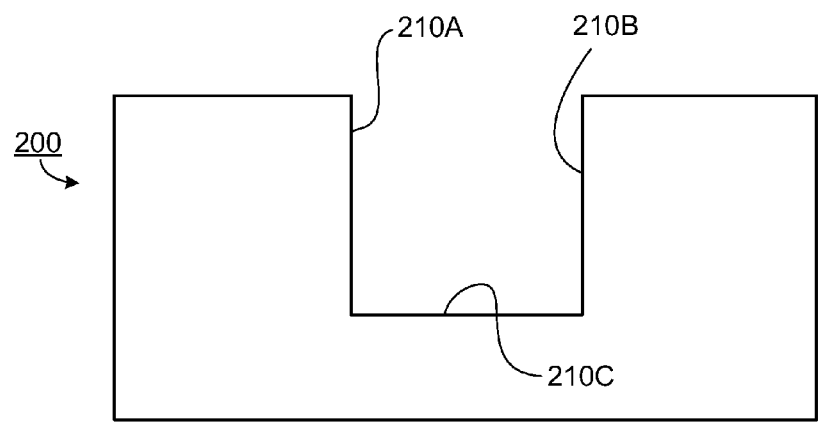

FIGS. 2A and 2B show partial top and cross-sectional views, respectively of a semiconductor article 200. As shown in FIG. 2B, article 200 has been cut to expose a cross-section 210 with sidewalls 210A and 210B and bottom wall 210C. Although not shown in FIGS. 2A and 2B, semiconductor article 200 includes many layers of different materials, and, in some instances, multiple different materials within the same layer.

An example of such detection involves the detection of voids. During the fabrication of a semiconductor article, voids in certain features or layers may be inadvertently formed. In some embodiments, the voids can undesirably impact the properties (e.g., electrical, mechanical) of the feature and/or the overall device. Subsequent processing steps may open the void, and the void may, for example, fill with liquid and/or gaseous components. This can cause corrosion of the underlying structures, particle defects and/or residue defects on the surrounding wafer surface. Ultimately, the presence of voids can result in deviation of electrical and/or mechanical properties from desired (e.g., designed) values.

Another example of the defect detection of a semiconductor article involves overlay shift registration. Overlay shift registration generally refers to the alignment of a feature of a given layer of a semiconductor article with a feature in a different layer of the semiconductor article. As noted above, the formation of a semiconductor article generally involves the proper formation of many layers. Typically, a semiconductor article contains well over 20 layers. Often, each layer can contain multiple different features, each of which is desirably located with high precision so that the semiconductor article can function properly. As an example, a semiconductor article can contain lateral features, such as electrically conductive wires, which are in different layers and connected to each other by a via. In general, it is desirable to have features within the semiconductor article properly aligned with each other.

An additional example of defect detection involves critical dimension metrology. Critical dimension metrology refers to the measurement of the linear dimensions of features in a semiconductor article that can have a critical impact on the performance of the device. Examples of such features can include lines (e.g., lines of electrically conductive material, lines of electrically semiconductive conductive material, lines of electrically non-conductive material). A semiconductor article can contain one or more features having a size dimension of 20 nm or less (e.g., 10 nm or less, five nm or less, four nm or less, three nm or less, two nm or less, one nm or less). In some embodiments, the size of the feature is measured multiple times to provide statistical information regarding the size of the feature. Critical dimension measurements frequently involve, e.g., the determination of the length of a patterned feature on a wafer, for example. Wafers (containing multiple dies, with each die forming a semiconductor article) may be selected at random from a fabrication line for inspection, or all wafers on the line can be inspected. An imaging instrument can be used to measure selected critical dimensions at a relatively high throughput rate. If the measured critical dimension does not fall within acceptable limits, the wafer may be discarded. If multiple samples originating from a particular fabrication machine have critical dimensions outside acceptable limits, the machine may be taken out of service, or its operating parameters changed.

A further example of defect detection involves line edge roughness and/or line width roughness. Line edge roughness generally refers to the roughness of the edge of a line of material in a semiconductor article, and line width roughness generally refers to the roughness of the width of a line of material in a semiconductor article. It can be desirable to understand these values to determine whether actual or potential problems exist in a given semiconductor article. For example, if adjacent lines formed of electrically conductive material have edges that bulge outward toward each other, the lines may contact each other resulting in a short. It can be desirable to understand the dimensions of line edge roughness and/or line width roughness to within five nm or less (e.g., four nm or less, three nm or less, two nm or less, one nm or less, 0.9 nm or less, 0.8 nm or less, 0.7 nm or less, 0.6 nm or less, 0.5 nm or less). Examples of sample inspection are disclosed, for example, in US 2007-0158558.

In some embodiments, the systems and methods can be used to modify (e.g., repair) a sample (e.g., to repair a region of the article at or near the portion of the article exposed by the cross-section). Such modification can involve gas assisted chemistry, which can be used to add material to and/or remove material to a sample (e.g., a given layer of the sample). As an example, gas assisted chemistry can be used for semiconductor circuit editing in which damaged or incorrectly fabricated circuits formed in semiconductor articles are repaired. Typically, circuit editing involves adding material to a circuit (e.g., to close a circuit that is open) and/or removing material from a circuit (e.g., to open a circuit that is closed). Gas assisted chemistry can also be used in photolithographic mask repair. Mask defects generally include an excess of mask material in a region of the mask where there should be no material, and/or an absence of mask material where material should be present. Thus, gas assisted chemistry can be used in mask repair to add and/or remove material from a mask as desired. Typically, gas assisted chemistry involves the use of a charged particle beam (e.g., ion beam, electron beam, both) that interacts with an appropriate gas (e.g., $Cl_2$, $O_2$, $I_2$, $XeF_2$, $F_2$, $CF_4$, $H_2O$, $XeF_2$, $F_2$, $CF_4$, $WF_6$). As another example, modification of a sample can involve sputtering. In some instances, when fabricating articles, it can be desirable during certain steps to remove materials (e.g., when removing undesired material from a circuit to edit the circuit, when repairing a mask). An ion beam can be used for this purpose where the ion beam sputters material from the sample. In particular, an ion beam generated via the interaction of gas atoms with a gas field ion source as described herein can be used for sputtering a sample. Although He gas ions may be used, it is typically preferable to use heavier ions (e.g., Ne gas ions, Ar gas ions, Kr gas ions, Xe gas ions) to remove material. During the removal of material, the ion beam is focused on the region of the sample where the material to be removed is located. Examples of sample modification are disclosed, for example, in US 2007-0158558.

While the foregoing discussion relates to samples in the form of semiconductor articles, more generally, any type of sample can be used. Examples of samples include biological samples (e.g., tissue, nucleic acids, proteins, carbohydrates, lipids and cell membranes), pharmaceutical samples (e.g., a small molecule drug), frozen water (e.g., ice), read/write heads used in magnetic storage devices, and metal and alloy samples.

Samples, Sample Inspection and Sample Modification are disclosed in, for example, US 2007-0158558.

Other Embodiments

While certain embodiments have been described, other embodiments are possible.

As an example, while embodiments have been described in which an isotope (a minority isotope, a light isotope) is used, in some embodiments multiple isotopes (e.g., two isotopes, three isotopes, four isotopes, five isotopes, etc.) can be used.

As another example, while embodiments have been described in which a single detector is used, optionally multiple detectors (e.g., two, three, four, five, six, etc.) may be used.

As a further example, while embodiments have been described in which a detector is positioned on the same side of a sample as the charged particle source, in certain embodiments, a detector may be positioned on the opposite side of the sample from the charged particle source. In such embodiments, it may be of interest, for example, to detect electrons that are generated by He ions that are transmitted by (e.g., transmitted through) the sample. Such electrons are typically generated on the backside surface of the sample. Optionally, a system may include one or more detectors located on the same side of the sample as the charged particle source, as well as one or more detectors located on the opposite side of the sample relative to the charged particle source.

As an additional example, in some embodiments, the electrons that are detected pass through at least a portion of (e.g., through the final lens of) the ion optics. Because the ion optics typically include one or more lenses, such detection configurations are often referred to as through lens detectors.

In general, various aspects of the foregoing embodiments can be combined as desired.

Other embodiments are covered by the claims.

What is claimed is:

1. A method, comprising:
   using a gas field ion source to form a beam of ions of an isotope of a noble gas; and
   using the isotope of the noble gas in the beam of ions to investigate or modify a sample,
   wherein the isotope of the noble gas is Ne-20, and an amount of the ions of the isotope of the noble gas is greater than a natural abundance of the isotope of the noble gas.

2. The method of claim 1, wherein the amount of the ions of the isotope of the noble gas is greater than 95%.

3. The method of claim 2, further comprising exposing the noble gas to the gas field ion source to form the ion beam, wherein at least 95% of the atoms in the gas are Ne-20 atoms.

4. The method of claim 3, further comprising:
   exposing the sample to the ion beam to cause particles to leave the sample; and
   detecting particles to determine information about the sample.

5. The method of claim 4 further comprising passing the ions through ion optics.

6. A method, comprising:
   using a gas field ion source to form a beam of ions of an isotope of a noble gas; and
   using the isotope of the noble gas in the beam of ions to investigate or modify a sample,
   wherein the isotope of the noble gas is Ne-21, and an amount of the ions of the isotope of the noble gas is greater than a natural abundance of the isotope of the noble gas.

7. The method of claim 6, wherein the amount of the ions of the isotope of the noble gas is greater than 95%.

8. The method of claim 7, further comprising exposing the noble gas to the gas field ion source to form the ion beam, wherein at least 95% of the atoms in the gas are Ne-21 atoms.

9. The method of claim 8, further comprising:
   exposing the sample to the ion beam to cause particles to leave the sample; and
   detecting particles to determine information about the sample.

10. The method of claim 9 further comprising passing the ions through ion optics.

11. A method, comprising:
    using a gas field ion source to form a beam of ions of an isotope of a noble gas; and
    using the isotope of the noble gas in the beam of ions to investigate or modify a sample,
    wherein the isotope of the noble gas is Ne-22, and an amount of the ions of the isotope of the noble gas is greater than a natural abundance of the isotope of the noble gas.

12. The method of claim 11, wherein the amount of the ions of the isotope of the noble gas is greater than 95%.

13. The method of claim 12, the method further comprising exposing the noble gas to the gas field ion source to form the ion beam, wherein at least 95% of the atoms in the gas are Ne-22 atoms.

14. The method of claim 13, further comprising:
    exposing the sample to the ion beam to cause particles to leave the sample; and
    detecting particles to determine information about the sample.

15. The method of claim 14, further comprising passing the ions through ion optics.

16. The method of claim 1, wherein the sample comprises a semiconductor article and the method repairs a circuit by adding material to the sample or removing material from the sample.

17. The method of claim 6, wherein the sample comprises a semiconductor article and the method repairs a circuit by adding material to the sample or removing material from the sample.

18. The method of claim 11, wherein the sample comprises a semiconductor article and the method repairs a circuit by adding material to the sample or removing material from the sample.

* * * * *